(12) United States Patent
Astle

(10) Patent No.: US 6,884,396 B2
(45) Date of Patent: Apr. 26, 2005

(54) PIPETTOR RESERVOIR FOR PARTICULATE-CONTAINING LIQUIDS

(76) Inventor: Thomas W. Astle, 607 Harborview Rd., Orange, CT (US) 06477

( * ) Notice: Subject to any disclaimer, the term of this patent is extended or adjusted under 35 U.S.C. 154(b) by 469 days.

(21) Appl. No.: 09/815,022

(22) Filed: Mar. 22, 2001

(65) Prior Publication Data

US 2002/0136666 A1 Sep. 26, 2002

(51) Int. Cl.⁷ .............................. B01L 3/02; B01L 3/00
(52) U.S. Cl. ...................................... 422/100; 422/102
(58) Field of Search .......................... 422/99, 100, 102, 422/104, 103

(56) References Cited

U.S. PATENT DOCUMENTS

| | | | | |
|---|---|---|---|---|
| 3,232,590 A | * | 2/1966 | Eckert | 261/97 |
| 4,948,564 A | * | 8/1990 | Root et al. | 422/101 |
| 5,866,825 A | * | 2/1999 | Moore et al. | 73/864.22 |
| 6,109,778 A | * | 8/2000 | Wilmer | 366/137 |
| 6,217,207 B1 | * | 4/2001 | Streich et al. | 366/137 |
| 6,234,664 B1 | * | 5/2001 | Tromley | 366/162.4 |
| 6,274,091 B1 | * | 8/2001 | Mohan et al. | 422/103 |
| 6,475,444 B1 | * | 11/2002 | Zimmermann et al. | 422/102 |
| 2002/0187078 A1 | * | 12/2002 | Al-Obeidi et al. | 422/102 |

* cited by examiner

Primary Examiner—Jill Warden
Assistant Examiner—Brian R. Gordon
(74) Attorney, Agent, or Firm—John H. Crozier

(57) ABSTRACT

In a preferred embodiment, a pipettor reservoir for particulate-containing liquid, including: a body portion; a shallow reservoir portion defined in an upper surface of the body portion; fluid-flow channels defined in the body portion to deliver the particulate-containing liquid from an inlet port to a plurality of openings defined in a bottom of the reservoir portion, the plurality of openings being arranged such as to agitate the particulate-containing liquid to keep particulate matter in suspension therein.

4 Claims, 3 Drawing Sheets

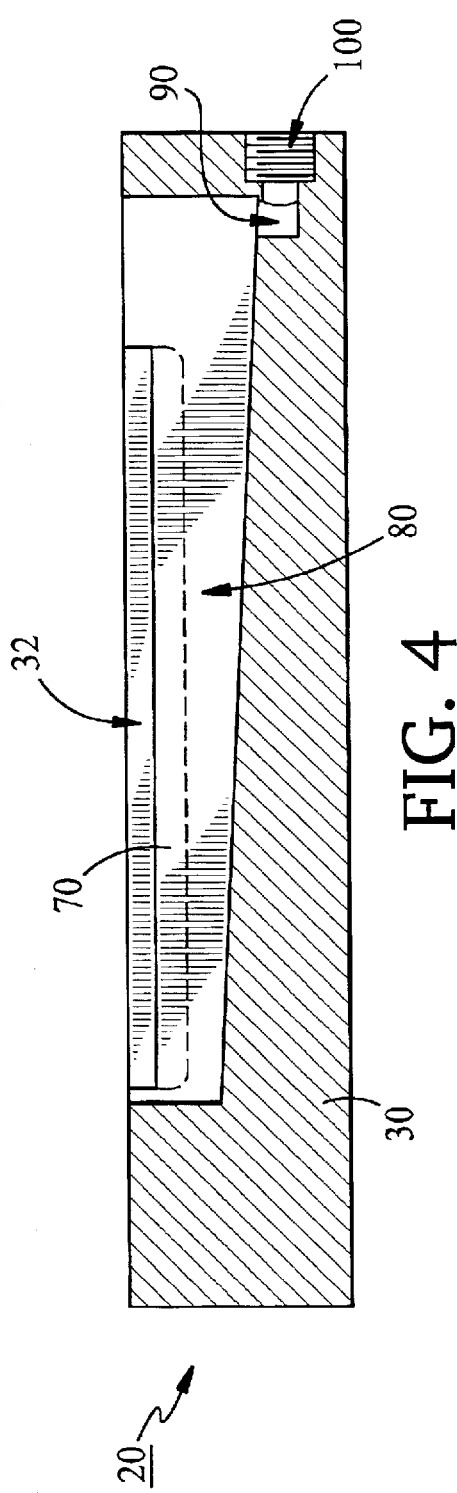
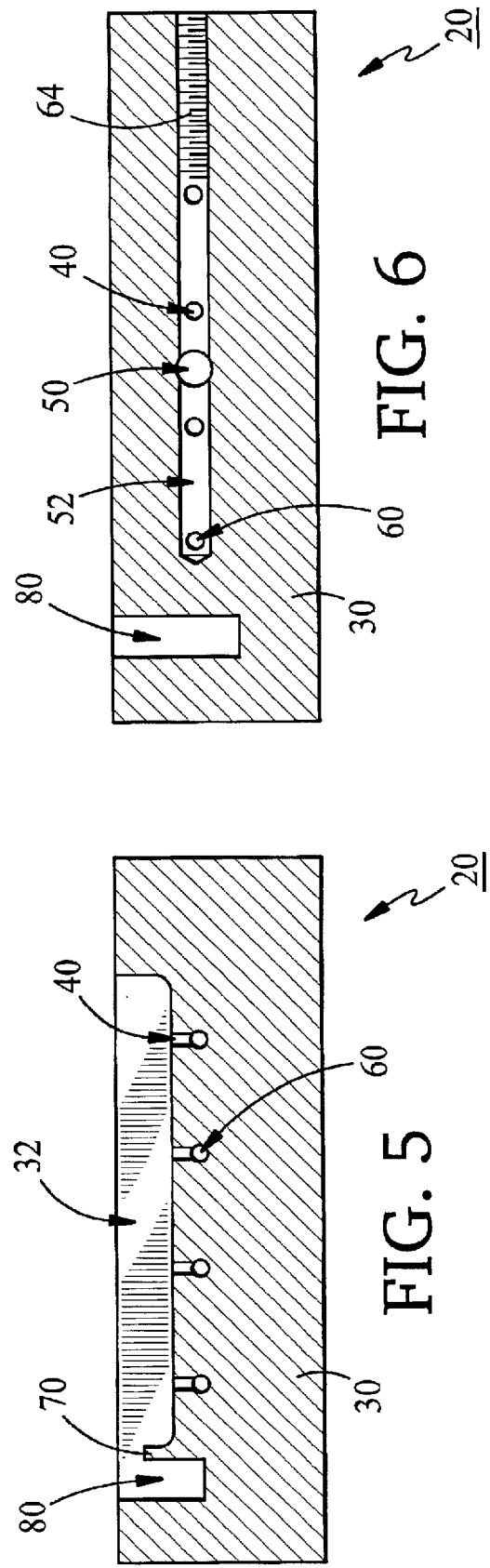

PIPETTOR RESERVOIR FOR PARTICULATE-CONTAINING LIQUIDS

BACKGROUND OF THE INVENTION

1. Field of the Invention

The present invention relates to bioassays generally and, more particularly, but not by way of limitation, to a novel pipettor reservoir for use with particulate-containing liquids.

2. Background Art

In the field of biotechnology, particulate matter is used in a variety of assays. The most common particulate matter is the use of living cells. Other applications are the use of coated particles, such as magnetic beads or radioactive particles. In high throughput systems, it is necessary to pipette liquid containing this particulate matter from a source reservoir to a receiving bioassay plate. A problem encountered in such systems is that the particulate matter tends to settle out of the liquid in which it is suspended. A common method of overcoming this tendency is the use of a magnetic stir bar within the reservoir, driven by an external magnet drive assembly. Various shakers and vibrators are also used.

In automated pipetting systems, a constant level source reservoir may be used. This is a weir-type reservoir that is included within the flow path of a peristaltic pump. The fluid is kept in motion between a large source reservoir and the constant level reservoir by the peristaltic pump. The agitation created by the flow is relied on to keep the particulate matter in suspension in the liquid.

The constant level reservoir has a relatively small depth and the liquid level is kept constant by an overflow weir. This allows the pipettor system to go to the same depth in the liquid for aspiration of the reagents. For use with the industry standard, 96- or 384-well pipettors, the horizontal dimensions of the reservoir surface area must measure approximately 3.4×5.0 inch. Depending on the mass of the particles, the flow through the reservoir may not keep them in suspension. There are normally "dead" spots in the corners of the reservoir or other areas of the reservoir outside of the main liquid path. A multi-well pipettor, 96 or 384 wells, will aspirate uniformly over the entire 3.4×5.0-inch surface area; however, the "dead" spots in the reservoir will not provide a uniform aspiration of particles in all 96 or 384 pipettor tips. This has a detrimental effect on the results of the assay.

Also, there is an increasing use of paramagnetic particles in various bioassays and the use of a magnetic stir bar is prohibited in these applications.

Accordingly, it is a principal object of the present invention to provide a source reservoir for pipetting in which the problem of settling of particulate matter suspended in a liquid is eliminated or greatly reduced.

A further object of the invention is to provide such a source reservoir in which "dead" spots are eliminated or greatly reduced.

An additional object of the invention is to provide such a source reservoir having a constant velocity of liquid flow in the various feed-way passages thereof Another object of the invention is to provide such a source reservoir that can be economically constructed using conventional manufacturing techniques.

Yet a further object of the invention is to provide a source reservoir that can be used satisfactorily with paramagnetic particulate materials.

Other objects of the present invention, as well as particular features, elements, and advantages thereof, will be elucidated in, or be apparent from, the following description and the accompanying drawing figure.

SUMMARY OF THE INVENTION

The present invention achieves the above objects, among others, by providing, in a preferred embodiment, a pipettor reservoir for particulate-containing liquid, comprising: a body portion; a shallow reservoir portion defined in an upper surface of said body portion; fluid-flow channels defined in said body portion to deliver said particulate-containing liquid from an inlet port to a plurality of openings defined in a bottom of said reservoir portion, said plurality of openings being arranged such as to agitate said particulate-containing liquid to keep particulate matter in suspension therein.

BRIEF DESCRIPTION OF THE DRAWING

Understanding of the present invention and the various aspects thereof will be facilitated by reference to the accompanying drawing figures, provided for purposes of illustration only and not intended to define the scope of the invention, on which:

FIG. 4 is a side elevational view, in cross-section, taken along line "4—4" of FIG. 1.

FIG. 5 is an end elevational view, in cross-section, taken along line "5—5" of FIG. 1.

FIG. 6 is an end elevational view, in cross-section, taken along line "6—6" of FIG. 1.

DETAILED DESCRIPTION OF THE PREFERRED EMBODIMENTS

Figure 1:
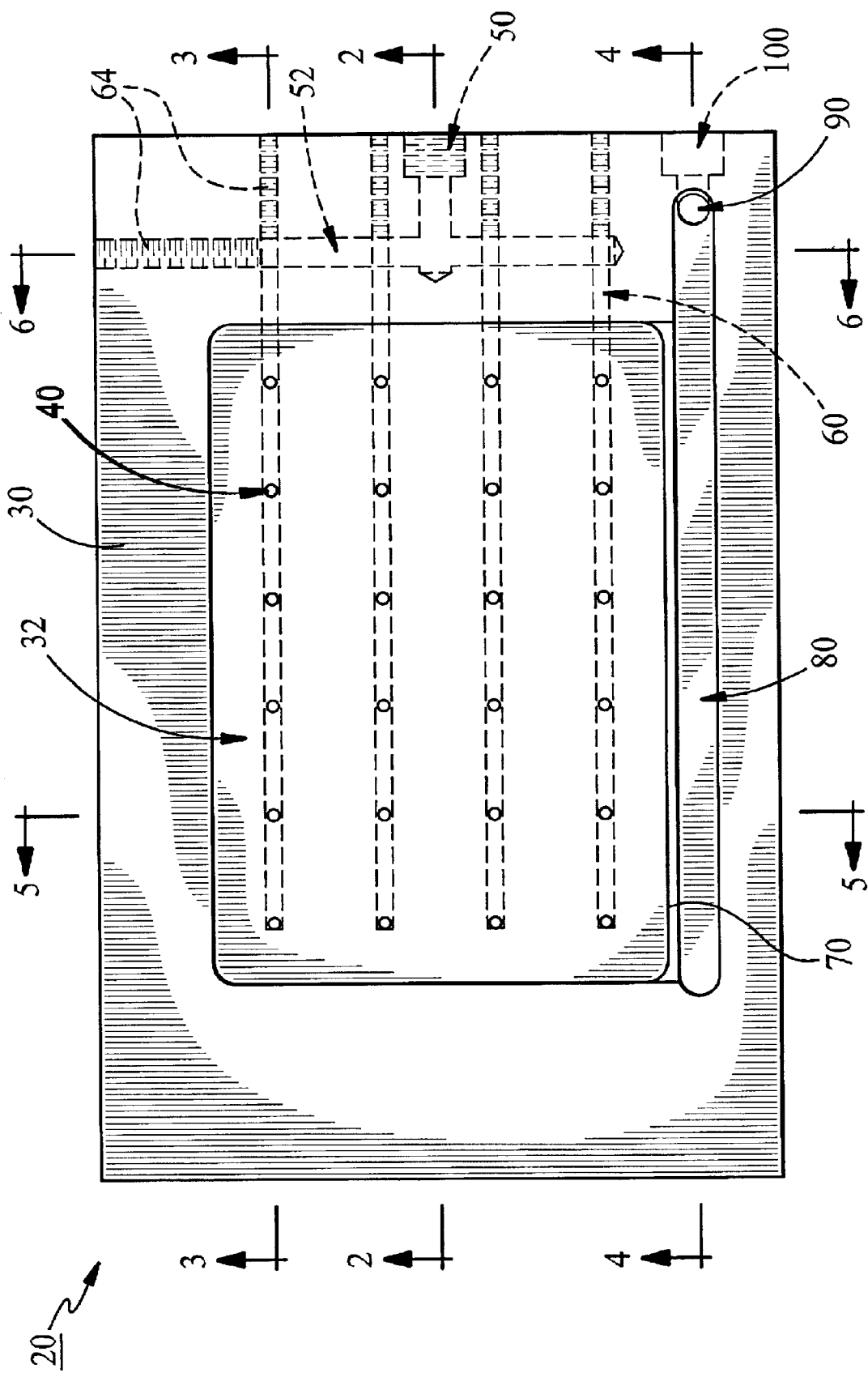
FIG. 1 is a top plan view of a source reservoir constructed according to the present invention.

Reference should now be made to the drawing figures on which similar or identical elements are given consistent identifying numerals throughout the various figures thereof, and on which parenthetical references to figure numbers direct the reader to the view(s) on which the element(s) being described is (are) best seen, although the element(s) may be seen on other figures also.

Figure 2:
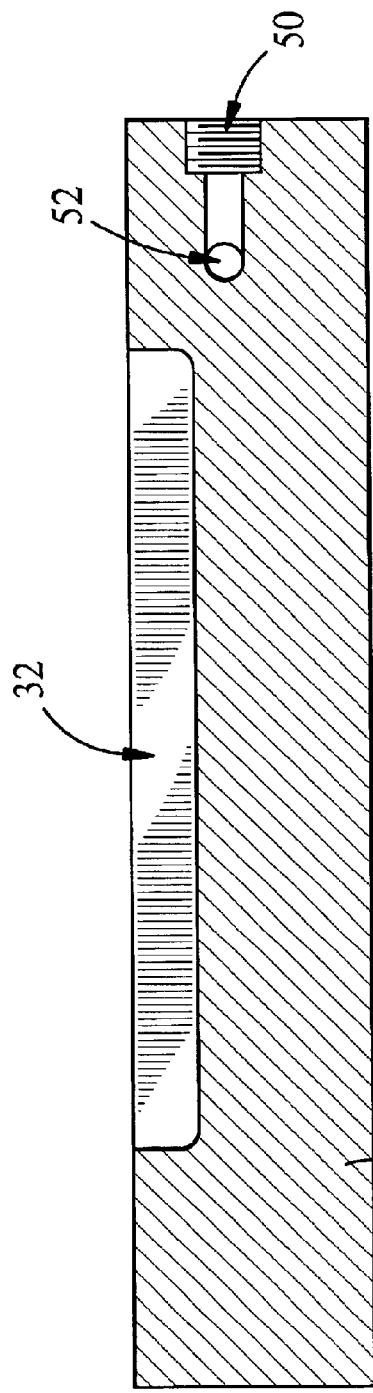
FIG. 2 is a side elevational view, in cross-section, taken along line "2—2" of FIG. 1.
Figure 3:
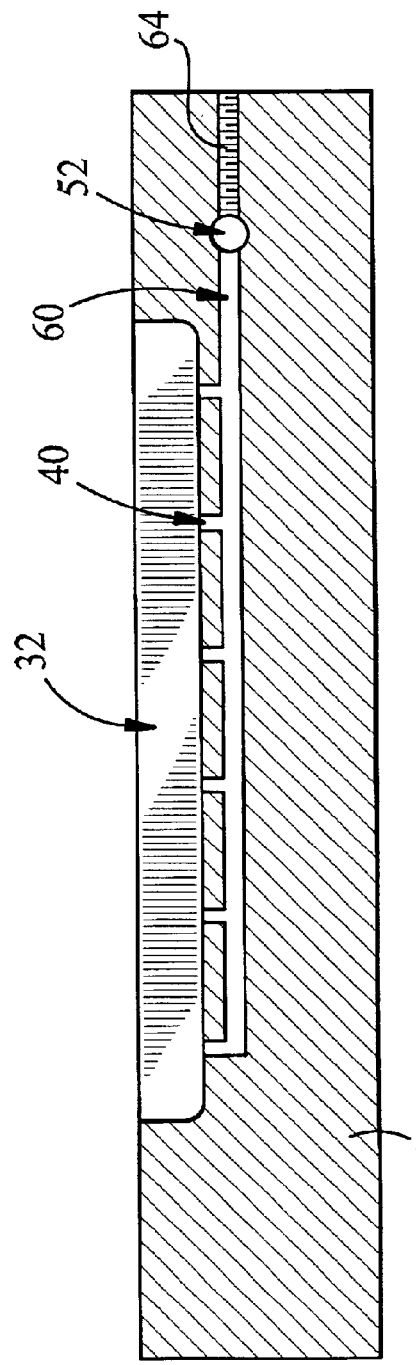
FIG. 3 is a side elevational view, in cross-section, taken along line "3—3" of FIG. 1.

Referring to all the drawing figures, but primarily to FIG. 1, there is illustrated a pipettor source reservoir, constructed according to the present invention, and generally indicated by the reference numeral 20. Pipettor source reservoir 20 has a rectangular body portion 30 and a rectangular reservoir portion 32 (FIG. 2), measuring, as noted above, about 3.4×5.0 inches, the pipettor source reservoir being formed in the upper surface of the rectangular body portion Other dimensions for reservoir portion 32 may be used as well depending on the application, the above dimensions being required for the standard 96- or 384-well pipettors.

Reservoir portion 32 has 24 small, vertical holes, as at 40, defined in the bottom thereof. Body 30 has defined therein an inlet port 50 connected to the middle of a main feed line header 52. Main feed line header 52 is connected to four feed lines, as at 60, each of which is connected to six vertical holes 40. Portions, as at 64, of main feed line header 52 and feed lines 60 are blocked, the portions that are now blocked having been formed in the drilling operation that formed the main feed header and the feed lines.

A horizontal weir 70 (FIGS. 4 and 5) extends along one side of reservoir portion 32 and has a vertical height terminating somewhat below the upper edge of the depressed central portion. A sloped drain channel 80 (FIG. 4) extends along the side of weir 70 opposite the side of the weir that is adjacent reservoir portion 32 and the lower end of sloped drain channel 80 terminates in a sump 90 (FIG. 4) connected to an outlet port 100.

In use, a liquid containing particulate matter, such as paramagnetic particles or living cells, is introduced through inlet port 50, flows through main feed header 52, flows through feed lines 60, and flows uniformly into reservoir portion 32 through holes 40. Weir 70 (FIGS. 4 and 5) maintains the level of liquid in reservoir portion 32 constant. Pipettor needles are inserted into the liquid in reservoir portion 32 a given and constant depth. Excess liquid flows over weir 70, into sloped drain channel 80 (FIG. 4) and out of source reservoir 20 through sump 90 and outlet port 100. Supply to inlet port 50 may be by means of a peristaltic pump (not shown) and outlet port 100 may be connected to the inlet side of the pump or to a main reservoir.

Pipettor source reservoir 20 is designed such that approximately the same linear velocity of flow in all flow passages is obtained in all liquid flow passages to prevent settling. For example, the cross-sectional area of main feed line header 52 is approximately one-half the area of inlet port 50, since the main feed line header has two branches. The combined cross-sectional area of two feed lines 60 is approximately equal to the cross-sectional area of main feed line header 52. The cross-sectional area of six vertical holes 40 is approximately equal to the cross-sectional area of a feed line 60. The generally equal spacing of vertical holes 40 across the bottom of depressed central portion 32 keeps the volume in constant agitation to prevent settling in any of what would otherwise be "dead" spots. Exact dimensions of the flow passages will depend on the nature of the particulate matter in suspension, but will be such that the particulate matter remains in suspension.

The use of single weir 70, as opposed to a full perimeter weir, maintains faster uniform flow out of reservoir portion 32. The depth of the liquid is kept shallow again for the purposes of a cross flow velocity sufficient to keep particles in suspension. This is accomplished by having the vertical height dimension of weir 70 above the bottom of reservoir portion 32 roughly two to five percent of the length of the reservoir portion.

The flow rate of the liquid, being delivered by the peristaltic pump, is a parameter that is adjustable to compensate for use with particles of different masses. Heavier magnetic beads may heed a higher flow velocity, to keep them in suspension, compared with living cells.

Pipettor source reservoir 20 and the various elements thereof may be economically constructed by conventional manufacturing methods. Materials of construction may be any that are suitable for the liquids and particulate being handled.

Terms such as "upper", "lower", "inner", "outer", "inwardly", "outwardly", "vertical", "horizontal", and the like, when used herein, refer to the positions of the respective elements shown on the accompanying drawing figures and the present invention is not necessarily limited to such positions.

It will thus be seen that the objects set forth above, among those elucidated in, or made apparent from, the preceding description, are efficiently attained and, since certain changes may be made in the above construction and method without departing from the scope of the invention, it is intended that all matter contained in the above description or shown on the accompanying drawing figures shall be interpreted as illustrative only and not in a limiting sense.

It is also to be understood that the following claims are intended to cover all of the generic and specific features of the invention herein described and all statements of the scope of the invention which, as a matter of language, might be said to fall therebetween.

The embodiments of the invention in which an exclusive property or privilege is claimed are defined as follows:

1. A pipettor reservoir for particulate-containing liquid, comprising:
   (a) a body portion;
   (b) a shallow, single reservoir portion defined in an upper surface of said body portion;
   (c) an inlet port defined in said body portion;
   (d) a plurality of openings defined in said body portion and opening into, a bottom of said single reservoir portion;
   (e) fluid-flow channels including feed lines defined in said body portion to deliver said particulate-containing liquid from said inlet port to said plurality of openings in said feed lines, said plurality of openings being arranged such as to agitate said particulate-containing liquid in said single reservoir portion to keep particulate matter in suspension therein; and
   f) said fluid-flow channels are sized to maintaining approximately equal flow rates sufficient to keep said particulate matter in suspension and the total cross-sectional area of said feed lines is approximately equal to the cross-sectional area of said inlet port.

2. The pipettor reservoir for particulate containing liquid, as defined in claim 1, further comprising: a single weir overflow disposed along one side of said single reservoir portion to maintain a constant liquid level in said reservoir portion, said single weir overflow being the only weir overflow in the device.

3. The pipettor reservoir for particulate containing liquid, as defined in claim 2, wherein: height of said single weir overflow above a bottom surface of said single reservoir portion is approximately two to five percent of length of said reservoir portion.

4. A pipettor reservoir for particulate-containing liquid, as defined in claim 1, wherein:
   (a) said inlet port is connected to a main feed line header;
   (b) said main feed line header has two branches, extending outwardly from where said inlet port is connected to said main feed line header;
   (c) each of said two branches is connected to two feed lines;
   (d) each of said two feed lines is connected to six openings defined in a bottom of said single reservoir;
   (e) cross-sectional area of each of said two branches is approximately one-half cross-sectional area of said inlet port;
   (f) combined cross-sectional area of said two feed lines is approximately equal to cross-sectional area of one of said two branches; and
   (g) combined cross-sectional area of said six openings is approximately equal to cross-sectional area of one of said two feed lines.

* * * * *